(12) United States Patent
Pruche

(10) Patent No.: US 6,723,136 B2
(45) Date of Patent: Apr. 20, 2004

(54) COLORATION COMPOSITION, PROCESS FOR OBTAINING THE SAME AND ITS USE FOR THE COLORATION OF KERATIN FIBRES

(75) Inventor: Francis Pruche, Senlis (FR)

(73) Assignee: L'Oreal, Paris (FR)

( * ) Notice: Subject to any disclaimer, the term of this patent is extended or adjusted under 35 U.S.C. 154(b) by 238 days.

(21) Appl. No.: 10/000,222

(22) Filed: Dec. 4, 2001

(65) Prior Publication Data

US 2002/0124330 A1 Sep. 12, 2002

(30) Foreign Application Priority Data

Dec. 4, 2000 (FR) .............................. 00 15695

(51) Int. Cl.$^7$ ................................ A61K 7/13
(52) U.S. Cl. ............... 8/405; 8/406; 8/407; 8/410; 8/412; 8/424; 8/435; 8/594; 8/596; 8/600; 8/601; 8/628; 8/629
(58) Field of Search ............. 8/405, 406, 407, 8/410, 412, 424, 435, 594, 596, 600, 601, 628, 629

(56) References Cited

U.S. PATENT DOCUMENTS 6,004,355 A * 12/1999 Dias et al. ............... 8/406

FOREIGN PATENT DOCUMENTS

| DE | 2 222 001 | 11/1973 |
| DE | 198 59 682 A1 | 6/2000 |
| EP | 0 621 029 A1 | 10/1994 |
| EP | 0 642 783 A1 | 3/1995 |
| FR | 2 748 274 | 11/1997 |
| GB | 2 307 175 A | 5/1997 |

* cited by examiner

*Primary Examiner*—Yogendra N. Gupta
*Assistant Examiner*—Eisa Elhilo
(74) *Attorney, Agent, or Firm*—Oblon, Spivak, McClelland, Maier & Neustadt, P.C.

(57) ABSTRACT

A composition for coloring keratin fibers comprises, a physiologically acceptable medium and an efficacious quantity of at least one coloring material precursor selected from the compounds containing at least one aromatic ring having at least two hydroxyl groups borne by two adjacent carbon atoms of the aromatic ring, an efficacious quantity of at least one oxidation base of the para or ortho type selected from the aromatic amines, and an efficacious quantity of a catalytic system comprising a first constituent selected from the group consisting of salts and oxides of Mn(II) and/or Zn(II) and their mixtures, and a second constituent selected from the group consisting of alkali hydrogen carbonates, alkaline earth hydrogen carbonates and their mixtures. Keratin fibers may be colored by the application of this composition thereto.

57 Claims, No Drawings

COLORATION COMPOSITION, PROCESS FOR OBTAINING THE SAME AND ITS USE FOR THE COLORATION OF KERATIN FIBRES

FIELD OF THE INVENTION

The present invention relates to a colouring composition for keratin fibres, a process for obtaining such a colouring composition and its use for the coloration of keratin fibres.

More particularly, the present invention relates to a colouring composition for hair, which after application to the latter, gives an original colour tint and makes it possible to increase the retention of the colour on the hair.

DISCUSSION OF THE BACKGROUND

In the field of the coloration of keratin fibres such as hair, eyelashes, eyebrows and bristles, the use of dye compositions containing oxidation bases such as p-phenylene diamines and ortho- or para-aminophenols to dye the keratin fibres, in particular human hair is well-known.

It is also known that the tints obtained with these oxidation bases can be varied by combining them with couplers, also called coloration modifiers, such as aromatic meta-diamines, meta-aminophenols, meta-diphenols and dihydroxyindole derivatives.

The revelation of the coloration of these compositions requires the use of an oxidising agent selected from, for example, hydrogen peroxide, urea peroxide, alkali metal bromates, persalts, such as the perborates and the persulfates, hydrogen peroxide being particularly preferred.

Enzymatic catalysts are also used to activate the coloration of colouring material precursors. Thus, the coloration of polyphenols is activated by oxidation in the presence of natural polyphenol oxidase. As an example, catechol in the presence of natural polyphenol oxidase gives an orangeish yellow colour and dihydroxyphenylalanine (L-DOPA) gives melanine. The principal advantage of these enzymatic catalysts consists in the production of colour pigments and original tints without the use of oxidants. However, the major disadvantage of this coloration process lies in the severe limitations to the use of enzymes on account of fears raised as to their harmlessness, their stability in the compositions, their reproducibility, their price and their often necessary immobilisation.

These compositions give results which are not totally satisfactory as far as retention and colour are concerned.

It is hence desirable to have available dye compositions which, as hair colouring materials give excellent results from the point of view of both colour and retention and for which it is possible to do without the use of conventional oxidising agents, in particular hydrogen peroxide or the use of enzymatic systems for the revelation of coloration.

SUMMARY OF THE INVENTION

The applicant has found, quite surprisingly, that it is possible to attain this goal with a composition which comprises a colouring material precursor selected from the compounds containing at least one aromatic ring having at least two hydroxyl groups borne by two adjacent carbon atoms of the aromatic ring, an oxidation base of the para or ortho type selected from the aromatic amines, and a chemical catalytic system comprising a first constituent selected from the salts and oxides of Mn(II) and/or Zn(II) and their mixtures, and a second constituent selected from the alkali hydrogen carbonates, the alkaline earth hydrogen carbonates and their mixtures.

Thus, the chemical catalytic system present in the composition of the invention behaves like a pseudo-oxidase capable of mimicking the oxidase activity without the disadvantages associated with the use of an enzymatic system.

In particular, this coloration composition, designed in particular for the coloration of keratin fibres, does not require the presence of enzymes or hydrogen peroxide.

The present invention also relates to a process for revealing the coloration of a slightly coloured or colourless base composition comprising at least one colouring material precursor by oxidation and at least one oxidation base to tint the coloration obtained which consists of adding to the base composition a purely chemical catalytic system and of placing the base composition supplemented with the catalytic system in the presence of a medium containing or generating oxygen.

The present invention also relates to a coloration process for keratin fibres using a composition such as that defined above.

Finally, the present invention relates to packaged and galenic forms of the colouring composition or constituents of the colouring composition according to the invention.

DETAILED DESCRIPTION OF THE INVENTION

The composition for the coloration of the skin and/or keratin fibres according to the invention comprises, in a physiologically acceptable medium, an efficacious quantity of at least one colouring material precursor selected from the compounds containing at least one aromatic ring having at least two hydroxyl groups (OH) borne by two adjacent carbon atoms of the aromatic ring, an efficacious quantity of at least one oxidation base of the para or ortho type selected from the aromatic amines, and an efficacious quantity of a catalytic system comprising a first constituent selected from the salts and oxides of Mn(II) and/or Zn(II) and their mixtures, and a second constituent selected from the alkali hydrogen carbonates, the alkaline earth hydrogen carbonates and their mixtures, the proportions of the first constituent and the second constituent being such that:

$$\frac{[Mn(II)]}{[HCO_3]} \leq 1 \text{ with } [Mn(II)] \neq 0$$

$$\frac{[Zn(II)]}{[HCO_3]} \leq 1 \text{ with } [Zn(II)] \neq 0$$

$$\frac{[Mn(II)] + [Zn(II)]}{[HCO_3]} \leq 1 \text{ with } [Mn(II)] \text{ and } [Zn(II)] \neq 0$$

where [Mn(II)], [Zn(II)] and [HCO$_3$] respectively represent the molar concentrations of Mn(II), Zn(II) and HCO$_3$ in the composition. In general, the ratio $$\frac{[Mn(II)]}{[HCO_3]}$$

varies from $10^{-5}$ to $10^{-1}$, and preferably from $10^{-3}$ to $10^{-2}$ and is typically of the order of $5 \times 10^{-3}$.

In the case where a salt or an oxide of Zn(II) alone is used, the ratio $$\frac{[Zn(II)]}{[HCO3]}$$

is usually of the order of 10 to 100 fold higher than when a salt or oxide of Mn(II) alone is used.

Typically, this ratio is $10^{-4}$ or more, preferably $10^{-3}$ or more, and preferably of the order of $5\times10^{-1}$.

In the case of a mixture of Mn(II) and Zn(II), the ratio usually varies from $10^{-5}$, to $10^{-1}$, preferably $10^{-3}$ to $10^{-2}$, a higher ratio being selected when the proportion of Zn(II) in the mixture is increased.

Usually, the molar concentration of Mn(II), Zn(II) or Mn(II)+Zn(II) in the final composition varies from $10^{-3}$ to 10 mM/l, and preferably from $10^{-2}$ to 1 mM/l.

When one or more salts or oxides of Mn(II) only is/are used, the molar concentration of Mn(II) in the final composition is typically $10^{-3}$ to $10^{-1}$ mM/l, and preferably from $10^{-2}$ to $10^{-1}$ mM/l.

Preferably, when the catalytic system contains one or more salts or oxides of Zn(II) only, the concentration of Zn(II) in the final composition is $5\times10^{-2}$ to 10 mM/l, and preferably from $5\times10^{-1}$ to 1 mM/l.

Of the salts of Mn(II) and Zn(II) suitable for the present invention, mention may be made of chloride, fluoride, iodide, sulfate, phosphate, nitrate and perchlorate, carboxylic acid salts and their mixtures.

As examples, mention may be made of manganese chloride, manganese carbonate (for example rhodochrosite), Mn(II) difluoride, Mn(II) tetrahydrate acetate, Mn(II) trihydrate lactate, Mn(II) phosphate, Mn(II) iodide, Mn(II) trihydrate nitrate, Mn(II) bromide and Mn(II) tetrahydrate perchlorate and Mn(II) sulfate monohydrate.

Particularly preferred salts are $MnCl_2$ and $ZnCl_2$.

The carboxylic acid salts also include hydroxylated carboxylic acid salts such as gluconate.

Of the alkaline and alkaline earth hydrogen carbonates, mention may be made of the hydrogen carbonates of Na, K, Mg, Ca and their mixtures, and preferably sodium hydrogen carbonate.

As previously indicated, the chemical catalytic system according to the invention constitutes a specific pseudo-oxidase which makes possible the oxidation of ortho-diphenols in the presence of oxygen as certain natural enzymatic catalysts having a polyphenol oxidase activity would do;

On the other hand, the catalytic system according to the invention has no pseudo-catalase activity in the sense that it does not cause the dismutation of 0.3% by weight hydrogen peroxide (i.e. 1 volume of oxygen).

The colouring material precursors of the compositions of the invention are compounds or mixtures of compounds containing at least one aromatic ring, preferably a benzene ring, containing at least two hydroxyl groups (OH) borne by two adjacent carbon atoms on the aromatic ring.

The aromatic ring may be a condensed aromatic ring optionally containing one or more heteroatoms such as naphthalene, tetrahydronaphthalene, indane, indene, anthracene, phenanthrene, indole, isoindole, indoline, isoindoline, benzofuran, dihydrobenzofuran, chroman, isochroman, chromene, isochromene, quinoline, tetrahydroquinoline and isoquinoline.

Preferably, the colouring material precursors according to the invention can be represented by formula (I):

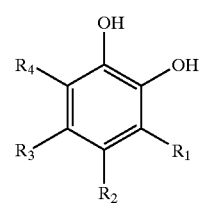

in which the substituents $R_1$ to $R_4$, identical or different, represent hydrogen, halogen, hydroxyl, carboxyl, alkyl carboxylate, optionally substituted amino, optionally substituted linear or branched alkyl, optionally substituted linear or branched alkenyl, optionally substituted cycloalkyl, alkoxy, alkoxyalkyl, alkoxyaryl, the aryl group being optionally substituted, aryl, substituted aryl, optionally substituted heterocyclic radical, a radical containing one or more silicon atoms in which two of the substituents $R_1$ to $R_4$ form together a saturated or unsaturated ring optionally containing one or more heteroatoms and optionally condensed with one or more saturated or unsaturated rings optionally containing one or more heteroatoms.

The optionally condensed saturated or unsaturated rings may also be optionally substituted.

The alkyl radicals are usually $C_1-C_{10}$ alkyl radicals, and preferably $C_1-C_6$ alkyl radicals such as methyl, ethyl, propyl, butyl, pentyl and hexyl.

The alkoxy radicals are usually $C_1-C_{20}$ alkoxy radicals, such as methoxy, ethoxy, propoxy and butoxy.

The alkoxyalkyl radicals are preferably $C_1-C_{20}$ alkoxy $C_1-C_{20}$ alkyl radicals such as methoxymethyl, ethoxymethyl, methoxyethyl, ethoxyethyl, etc.

The cycloalkyl radicals are usually $C_4-C_8$ cycloalkyl radicals, preferably cyclopentyl and cyclohexyl radicals. The cycloalkyl radicals may be substituted cycloalkyl radicals, in particular by alkyl, alkoxy, carboxylic acid, hydroxyl, amine and ketone groups.

The alkenyl radicals are preferably $C_2-C_{20}$ radicals, such as ethylene, propylene, butylene, pentylene, 2-methylpropylene and decylene.

The radicals containing one or more silicon atoms are preferably polydimethylsiloxane, polydiphenylsiloxane, polydimethylphenylsiloxane and stearoxydimethicone radicals.

The heterocyclic radicals are usually radicals comprising one or more heteroatoms selected from O, N and S, preferably O or N, optionally substituted by one or more alkyl, alkoxy, carboxylic acid, hydroxyl, amine or ketone groups.

Of the preferred heterocyclic radicals, mention may be made of the furyl, pyranyl, pyrrolyl, imidazolyl, pyrazolyl, pyridyl, thienyl groups.

Also preferably, the heterocyclic groups are condensed groups such as benzofuranyl, chromenyl, xanthenyl, indolyl, isoindolyl, quinolyl, isoquinolyl, chromanyl, isochromanyl, indolinyl, isoindolinyl, coumarinyl, isocoumarinyl, these groups being possibly substituted, in particular by one or more OH groups.

The preferred colouring material precursors are:
the flavanols such as catechol and epicatechol gallate,
the flavonols such as quercetin,
the anthocyanidines such as paeonidin,
the anthocyanines, for example oenin,
the hydroxybenzoates, for example gallic acid salts,
the flavones like luteolin,
the iridoils like oleuropein, these products being possibly glycosylated (for example glucosylated) and/or in the form of oligomers (procyanidines), the hydroxystilbene, for example tetrahydroxy-3,3',4,5'-stilbene, optionally glycosylated (for example glucosylated)

3,4-dihydroxyphenylalanine and its derivatives 2,3-dihydroxyphenylalanine and its derivatives 4,5-dihydroxyphenylalanine and its derivatives 4,5-dihydroxyindole and its derivatives 5,6-dihydroxyindole and its derivatives 6,7-dihydroxyindole and its derivatives 2,3-dihydroxyindole and its derivatives dihydroxycinnamates such as caffeic acid and chlorogenic acid hydroxycoumarins hydroxyisocoumarins hydroxycoumarones hydroxyisocoumarones hydroxychalcones hydroxychromones anthocyans quinones hydroxyxanthones 1,2-dihydroxybenzenes 1,2,4-trihydroxybenzenes 1,2,3-trihydroxybenzenes 2,4,5-trihydroxytoluene 5,6-dihydroxyindoline, and mixtures of these latter.

When the colouring material precursors exist in D and L forms, the two forms can be used in the compositions of the invention, as well as the racemates.

The quantity of colouring material precursors in the final composition must be sufficient to produce a visible coloration. This quantity may vary within wide limits as a function of the nature of the precursor and of the desired intensity of coloration.

In general, a suitable coloration is obtained when the colouring material precursor represents at least 0.001% by weight of the composition.

By varying the nature of the different colouring material precursors and their proportions in the composition, it is possible to vary the colour of the final composition. In this way a palette of colours is obtained.

For example, with a 1/10 ratio of chlorogenic acid and catechol, a light ibrown colour is obtained and with a 1/1 ratio a mahogany colour is produced.

The polymers formed in particular with catechol, gallic acid and their derivatives (tannins) have antimicrobial properties by imprisonment of the micro-organisms during the polymerisation. These tannins also have valuable astringent properties for the skin.

The colorant precursors may be extracted from plants, fruits, citrus fruits, vegetables and mixtures of these extracts which contain many polyphenols such as previously defined.

Of the plant extracts mention may be made of rose and tea extracts.

Of the fruit extracts, mention may be made of apple, grape (in particular grape seeds) and banana extracts.

Of the vegetable extracts, mention may be made of potato extract.

It is also possible to use mixtures of plant and/or fruit extracts such as mixtures of apple and tea extracts and mixtures of grape and apple extracts.

Depending on the parts of the fruits used, for example pulp or seeds of the grape, the coloration obtained is different.

The oxidation bases of the para or ortho type are compounds which are not themselves colouring materials but which form a colouring material by a process of oxidative condensation, either with themselves or in the presence of a coupler or modifier. They bear functional groups, either two amino groups or an amino group and a hydroxy group in a para or ortho position to each other.

The nature of these oxidation bases is not critical. They can be selected in particular from the ortho and para phenylenediamines, the double bases, the ortho and para aminophenols, the heterocyclic bases as well as the addition salts of all of these compounds with an acid.

As para phenylenediamines, particular mention may be made of the para phenylene diamines of the following formula (II) and their addition salts with an acid:

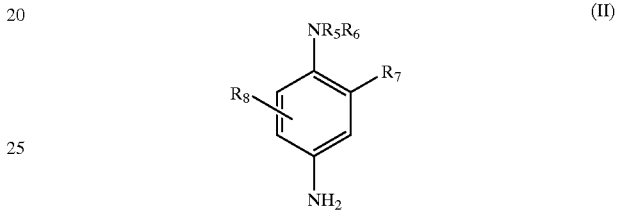

in which:

$R_5$ represents hydrogen, $C_1$–$C_4$ alkyl, $C_1$–$C_4$ monohydroxyalkyl, $C_2$–$C_4$ polyhydroxyalkyl, $C_1$–$C_4$ alkoxy $C_1$–$C_4$ alkyl, $C_1$–$C_4$ alkyl substituted by a nitrogen-containing group, phenyl or 4'-aminophenyl;

$R_6$ represents hydrogen, a $C_1$–$C_4$ alkyl, $C_1$–$C_4$ monohydroxyalkyl or $C_2$–$C_4$ polyhydroxyalkyl, $C_1$–$C_4$ alkoxy $C_1$–$C_4$ alkyl or $C_1$–$C_4$ alkyl substituted by a nitrogen-containing group;

$R_7$ represents hydrogen, halogen such as chlorine, $C_1$–$C_4$ alkyl radical, sulfo, carboxy, $C_1$–$C_4$ monohydroxyalkyl or $C_1$–$C_4$ hydroxyalkoxy, $C_1$–$C_4$ acetylaminoalkoxy, $C_1$–$C_4$ mesylaminoalkoxy or $C_1$–$C_4$ carbamoylaminoalkoxy;

$R_8$ represents hydrogen, halogen or $C_1$–$C_4$ alkyl;

$R_5$ and $R_6$ may also form with the nitrogen atom which bears them a 5 or 6 membered nitrogen-containing heterocycle, optionally substituted by one or more alkyl, hydroxy or ureido groups.

Of the nitrogen-containing groups of formula (II) abov, particular mention may be made of amino, $C_1$–$C_4$ monoalkylamino, $C_1$–$C_4$ dialkylamino, $C_1$–$C_4$ trialkylamino, $C_1$–$C_4$ monohydroxyalkyl amino, imidazolinium and ammonium.

Of the nitrogen-containing groups of formula (II) above, particular mentionmay be made of amino, $C_1$–$C_4$ monoalkylamino, $C_1$–$C_4$ dialkylamino, $C_1$–$C_4$ trialkylamino, $C_1$–$C_4$ monohydroxyalkyl amino, imidazolinium and ammonium.

Of the para-phenylenediamines of formula (II) above, particular mention may be made of para-phenylenediamine, para-toluylenediamine, 2-chloro-para-phenylenediamine, 2,3-dimethyl para-phenylenediamine, 2,6-dimethyl para-phenylenediamine, 2,6-diethyl para-phenylenediamine, 2,5-dimethyl para-phenylenediamine, N,N-dimethyl para-phenylenediamine, N,N-diethyl para-phenylenediamine, N,N-dipropyl para-phenylenediamine, 4-amino-N,N-diethyl-3-methyl-aniline, N,N-bis-(β-hydroxyethyl)-paraphenylenediamine, 4-N,N-bis-(β-hydroxyethyl) amino-2-methyl-aniline, 4-N,N-bis-(β-hydroxyethyl) amino-2-chloro-aniline, 2-β-hydroxyethyl para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylene-diamine, N-(β-γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and their addition salts with an acid.

Of the para-phenylenediamines of formula (II) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-diethyl-para-phenylenediamine, 2,3-dimethyl-para-phenylenediamine, N,N bis-β-(hydroxyethyl)-para-phenylenediamine, 2-chloro-para-phenylenediamine, and their addition salts with an acid are very specially preferred.

According to the invention, double bases signifies compounds containing at least two aromatic nuclei bearing amino and/or hydroxyl groups.

Of the double bases which can be used as oxidation bases in the dye compositions in conformity with the invention, particular mention may be made of the compounds corresponding to the following formula (Ill) and their addition salts with an acid:

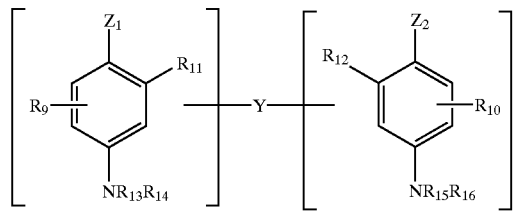

(III)

in which:
- $Z_1$ and $Z_2$, identical or different, represent a hydroxyl or —$NH_2$ radical which may be substituted by a $C_1$–$C_4$ alkyl radical or by a linking arm Y;
- the linking arm Y represents an alkylene chain comprising from 1 to 14 linear or branched carbon atoms which may be interrupted or terminated by one or more nitrogen-containing groups and/or by one or more heteroatoms such as oxygen, sulfur or nitrogen atoms, and optionally substituted by one or more hydroxyl or $C_1$–$C_6$ alkoxy radicals;
- $R_9$ and $R_{10}$ represent hydrogen or halogen, a $C_1$–$C_4$ alkyl radical, $C_1$–$C_4$ monohydroxyalkyl, $C_2$–$C_4$ polyhydroxyalkyl, $C_1$–$C_4$ aminoalkyl or a linking arm Y;
- $R_{11}$, $R_{12}$, $R_{13}$, $R_{14}$, $R_{15}$ and $R_{16}$, identical or different, represent hydrogen, a linking arm Y or a $C_1$–$C_4$ alkyl radical; it being understood that the compounds of formula (III) only bear a single linking arm Y per molecule.

Of the nitrogen-containing groups of formula (Ill) above, particular mention may be made of amino, $C_1$–$C_4$ monoalkylamino, $C_1$–$C_4$ dialkyl amino, $C_1$–$C_4$ trialkyl amino, $C_1$–$C_4$ monohydroxyalkyl amino, imidazolinium and ammonium.

Of the double bases of formula (Ill) above, more particular mention may be made of N,N'-bis-(β-hydroxyethyl) N,N'-bis-(4'-aminophenyl) 1,3-diamino propanol, N,N'-bis-(β-hydroxyethyl) N,N'-bis-(4'-aminophenyl) ethylenediamine, N,N'-bis-(4'-aminophenyl) tetramethylenediamine, N,N'-bis-(β-hydroxyethyl) N,N'-bis-(4'-aminophenyl) tetramethylenediamine, N,N'-bis-(4'-methyl-aminophenyl) tetramethylenediamine, N,N'-bis-(ethyl) N,N'-bis-(4'-amino, 3-methylphenyl) ethylenediamine, 1,8-bis-(2,5-diaminophenoxy)-3,5-dioxo-ocatane, and their addition salts with an acid.

Of these double bases of formula (II), N,N'-bis-(β-hydroxyethyl) N,N'-bis-(4'-aminophenyl) 1,3-diamino propanol, 1,8-bis-(2,5-diaminophenoxy)-3,5-dioxo-octane, or one of their addition salts with an acid are particularly preferred.

Of the para-aminophenols, particular mention may be made of the para-aminophenols corresponding to the following formula (IV), and their addition salts with an acid:

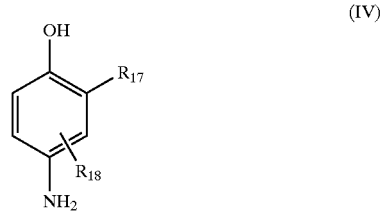

(IV)

in which:
- $R_{17}$ represents hydrogen, halogen such as fluorine, $C_1$–$C_4$ alkyl, $C_1$–$C_4$ monohydroxyalkyl, $C_1$–$C_4$ alkoxy $C_1$–$C_4$ alkyl or $C_1$–$C_4$ aminoalkyl, or $C_1$–$C_4$ hydroxyalkyl $C_1$–$C_4$ aminoalkyl, and
- $R_{18}$ represents hydrogen, halogen such as fluorine, $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $C_1$–$C_4$ hydroxyalkyl $C_1$–$C_4$ alkyl Of the para-aminophenols of formula (IV) above, more particular mention may be made of para-aminophenol, 4-amino-3-methyl-phenol, 4-amino-3-fluoro-phenol, 4-amino-3-hydroxymethyl phenol, 4-amino-2-methyl phenol, 4-amino-2-methoxymethyl phenol, 4-amino-2-aminomethyl phenol, 4-amino-2-(β-hydroxyethyl-aminomethyl) phenol, and their addition salts with an acid.

The ortho-aminophenols which can be used as oxidation bases in the framework of the present invention are selected in particular from 2-aminophenol, 2-amino-1-hydroxy-5-methyl-benzene, 2-amino-1-hydroxy-6-methyl-benzene, 5-acetamido-2-amino-phenol, and their addition salts with an acid.

Of the heterocyclic bases which can be used as oxidation bases in the dye compositions in conformity with the invention, more particular mention may be made of pyridine derivatives, pyrimidine derivatives, pyrazole derivatives and their addition salts with an acid.

Of the pyridine derivatives, more particular mention may be made of the compounds described for example in the patents GB-1026978 and GB-1153196, each of which is herein incorporated by reference, like 2,5-diamino pyridine, 2-(4-methoxyphenyl)amino-3-amino-pyridine, 2,3-diamino-6-methoxy pyridine, 2-(β-methoxyethyl) amino-3-amino-6-methoxy pyridine, 3,4-diamino pyridine and their addition salts with an acid.

Of the pyrimidine derivatives, more particular mention may be made of the compounds described for example in the German patent DE-2359399 or Japanese patents JP-88-169571 and JP-9110659 or patent applications WO 96/15765 each of which is herein incorporated by reference like 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the pyrazolo-pyrimidine derivatives such as those cited in the patent application FR-A-2 750 048, herein incorporated by reference, and of which mention may be made of pyrazolo-[1,5-a]-pyrimidine-3,7-diamine; 2,5-dimethyl-pyrazolo-[1,5-a]-pyrimidine-3,7-diamine, pyrazolo-[1,5-a]-pyrimidine-3,5-diamine; 2,7-dimethyl-pyrazolo-[1 ,5-a]-pyrimidine-3,5-diamine; 3-amino-pyrazolo-[1,5-a]-pyrimidin-7-ol; 3-amino-pyrazolo-[1,5-a]-pyrimidin-5-ol; 2-(3-amino-pyrazolo-[1,5-a]-pyrimidin-7-ylamino)-ethanol; 2-(7-amino-pyrazolo-[1,5-a]-pyrimidin-3-ylamino)-ethanol; 2-[(3-amino-pyrazolo-[1 ,5-a]-pyrimidin-7-yl)-(2-hydroxy-ethyl-amino)-ethanol; 2-[(7-amino-pyrazolo-[1,5-a]-pyrimidin-3-yl)-(2-hydroxy-ethyl-amino)-ethanol; 5,6-dimethyl-pyrazolo-[1,5-a]-pyrimidine-3,7-diamine; 2,5, N7,N7-tetramethyl-pyrazolo-[1,5-a]-pyrimidine-3 ,7-diamine; 3-amino-5-methyl-7-imidazolylpropylamino pyrazolo-[1,5-a]-pyrimidine; and their addition salts and their tautomeric forms, when a tautomeric equilibrium exists and their addition salts with an acid.

Of the pyrazole derivatives, more particular mention may be made of the compounds described in the patents DE-3843892, DE-4133957 and patent applications WO 94/08969, WO 94/08970, FR-A-2 733 749 and DE-19543988, each of which is incorporated by reference, like 4,5-diamino-1-methyl-pyrazole, 3,4-diamino-pyrazole, 4,5-diamino-1-(4'-chlorobenzyl)-pyrazole, 4,5-diamino-1,3-dimethylpyrazole, 4,5-diamino-3-methyl-1-phenyl pyrazole, 4,5-diamino-1-methyl-3-phenyl pyrazole, 4-amino-1,3-dimethyl-5-hydrazino-pyrazole, 1-benzyl-4,5-diamino-3-methyl pyrazole, 4,5-diamino-3-tert-butyl-1-methyl pyrazole, 4,5-diamino-1-tert-butyl-3-methyl pyrazole, 4,5-diamino-1-(β-hydroxyethyl)-pyrazole, 4,5-diamino-1-ethyl-3-methyl pyrazole, 4,5-diamino-1-ethyl-3-(4'-methoxyphenyl)-pyrazole, 4,5-diamino-1-ethyl-3-hydroxymethyl pyrazole, 4,5-diamino-3-hydroxymethyl-1-methyl pyrazole, 4,5-diamino-3-hydroxymethyl-1-isopropyl pyrazole, 4,5-diamino-3-methyl-1-isopropyl pyrazole, 4-amino-5-(2'-aminoethyl) amino-1,3-dimethyl pyrazole, 3,4,5-triamino pyrazole, 1-methyl-3,4,5-triamino-pyrazole, 3,5-diamino-1-methyl-4-methylamino-pyrazole, 3,5-diamino-4-(β-hydroxyethyl) amino-1-methyl-pyrazole, and their addition salts with an acid.

According to the present invention, the oxidation bases preferably represent from about 0.0005 to 12% by weight of the total weight of the composition and even more preferably from about 0.005 to 8% by weight of the total.

The physiologically acceptable medium is a solid or liquid medium not harmful to the colouring properties of the precursors nor to the catalytic effect of the catalytic system.

The physiologically acceptable medium is preferably a medium which dissolves the colouring material precursors.

Of the solvents for the precursors suitable for the formulation of the compositions according to the invention mention may be made of water, alcohols, polyol ethers and their mixtures.

Of these solvents, mention may be made, as examples, of the $C_1$–$C_4$ lower alkanols such as ethanol and isopropanol; the polyols or glycol ethers, such as 2-butoxyethanol, ethyleneglycol, glycerol, propyleneglycol, diethyleneglycol monoethylether and monomethylether as well as the aromatic alcohols like benzyl alcohol or phenoxyethanol and similar products or their mixtures.

The solvents are preferably present in proportions included between 1 to 40% by weight, and in particular between 5% and 30% by weight, of the total composition.

The solvents are preferably lower alkanols ($C_1$–$C_6$) such as ethanol and isopropanol and the alkane diols such as propylene glycol, glycerol and pentanediol.

The physiologically acceptable medium preferably consists of water (in particular distilled or demineralized water) or a water/alcohol mixture, in particular water/ethanol.

The quantity of alcohol in the water/alcohol may represent up to 80% by weight of the water/alcohol mixture, and preferably 1 to 50% by weight and, better still, 5 to 20% by weight.

The ready-to-use dye composition in conformity with the invention may contain one or more couplers selected from those conventionally used in oxidative dyeing and in particular from the meta-aminophenols, the metaphenylenediamines, the meta-diphenols, the naphthols and the heterocyclic couplers such as for example indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and their addition salts with an acid, these compounds being different from the ortho dihydroxylated compounds of the invention.

These couplers are selected more particularly from 2,4-diamino-1-(β-hydroxyethyloxy) benzene, 2-methyl 5-amino phenol, 5-N-(β-hydroxyethyl) amino 2-methyl phenol, 3-amino phenol, 1,3-dihydroxybenzene, 1,3-dihydroxy 2-methyl benzene, 4-chloro 1,3-dihydroxybenzene, 1,3-bis-(2,4-diaminophenoxy) propane, sesamol, 1-amino-2-methoxy-4,5-methylenedioxy benzene, α-naphthol, 6-hydroxyindoline, 2,6-dihydroxy 4-methyl pyridine, 1-H 3-methyl pyrazole 5-one, 1-phenyl 3-methyl pyrazol-5-one, 2-amino 3-hydroxypyridine, 3,6-dimethyl pyrazolo-[3,2-c]-1,2,4-triazole, 2,6-dimethyl-pyrazolo-[1,5-b]-1,2,4-triazole and their addition salts with an acid.

Usually the coupler(s) preferably represent(s) from approximately 0.0001 to 15% by weight of the total weight of the ready-to-use dye composition and even more preferably from about 0.001 to 10%.

The oxidation bases and the couplers constitute oxidation colouring materials. The addition salts with an acid of these oxidation colouring materials are selected in particular from the hydrochlorides, hydrobromides, sulfates, tartrates, lactates and acetates.

According to a preferred embodiment, the dye composition in conformity with the invention may in addition contain one or more direct colouring materials in particular for modifying the tints by enriching them with highlights. These direct colouring materials may in particular then be selected from nitro, azo or anthraquinone colouring materials, neutral, cationic or anionic colouring materials in a weight proportion of about 0.001 to 20% and preferably from 0.01 to 10% of the total weight of the composition.

The dye composition may also more particularly contain at least one surfactant, and preferably a non-ionic surfactant, in the proportion of at least 0.01% by weight. The surfactants may be selected from anionic, cationic, nonionic and amphoteric surfactants or their mixtures, and preferably from nonionic surfactants.

Of these surfactants, mention may be made of the alkylbenzenesulfonates, the alkylnaphthalenesulfonates, the sulfates, the ether sulfates and the sulfonates of fatty alcohols, the quaternary ammonium salts such as trimethylcetylammonium bromide and cetylpyridinium bromide; the ethanolamides of fatty acids optionally oxyethylenated; the polyoxyethylenated acids, alcohols or amines, the polyglycerolated alcohols, the polyoxyethylenated or polyglycerolated alkylphenols as well as the polyoxyethylenated alkylsulfates.

The quantities of surfactants present in the composition according to the invention may vary from 0.01 to 40% and preferably from 0.5 to 30% of the total weight of the composition.

The thickening agents that may be added to the compositions conforming to the invention may be selected from sodium alginate, gum arabic, cellulose derivatives, acrylic acid polymers, xanthan gum. It is also possible to use mineral thickening agents such as bentonite.

These thickening agents are preferably present in proportions included between 0.1 and 5% and in particular between 0.2 and 3% by weight of the total weight of the composition.

These compositions may also contain other cosmetically acceptable adjuvants such as, for example, penetration agents, perfumes, buffers, etc.

The compositions according to the invention may also contain any conventional adjuvant, in the usual proportions, which is not harmful to the desired properties, in particular to the colouring effect, of the compositions.

The colouring composition may also contain an efficacious quantity of other agents, moreover known to the prior art of oxidative coloration, such as various common adjuvants like UV filters, waxes, volatile or non-volatile silicones, cyclic or linear or branched, organo-modified or not (in particular by amine groups), preservatives, ceramides, pseudo-ceramides, vegetable, mineral or synthetic oils, vitamins or provitamins like panthenol, opacifiers, etc. . .

These organic UV filters may also be selected in particular from cinnamic derivatives; dibenzoylmethane derivatives; salicylic derivatives, camphor derivatives; triazine derivatives such as those described in the patent applications U.S. Pat. No. 4,367,390, EP-0.863.145, EP-0.5 17.104, EP-0.570.838, EP-0.796.851, EP-0.775.698, EP-0.878.469, EP-0.933.376 and EP 0.893.119, each of which is herein incorporated by reference; benzophenone derivatives; β, β'-diphenylacrylate derivatives, benzimidazole derivatives; bis-benzoazolyl derivatives such as those described in the patents EP-0.669.323 and U.S. Pat. No. 2,463,264, each of which is herein incorporated by reference; methylene bis-(hydroxyphenylbenzotriazole) derivatives such as those described in the applications U.S. Pat. No. 5,237,071, U.S. Pat. No. 5,166,355, GB-2303539, DE-19726184 and EP-0.893.119, each of which is herein incorporated by reference; p-aminobenzoic acid derivatives; the dimeric derivatives of α-alkylstyrene such as those described in the patent application DE-19855649, herein incorporated by reference; the hydrocarbon polymer filters and the silicone filters such as those described in particular in the application WO 93/04665, herein incorporated by reference. It is also possible to use pigments or even nanopigments (mean size of the primary particles; usually between 5 nm and 100 nm, preferably between 10 nm and 50 nm) of coated or uncoated metal oxides such as for example nanopigments of the oxides of titanium (amorphous or crystallized in the form of rutile and/or octahedrite), iron, zinc, zirconium or cerium which are all well-known UV photoprotective agents as such. Conventional coating agents are moreover aluminium and/or aluminium stearate. Such nanopigments of metal oxides, coated or uncoated are described in particular in the patent applications EP-0.518.772 and EP-0.518.773, each of which is herein incorporated by reference.

Naturally, the specialist skilled in the art will take care to select any additional compounds previously mentioned, such that the advantageous properties intrinsically attached to the dye composition according to the invention are not or not substantially impaired by the addition(s) envisaged.

Preferably, the compositions according to the invention are free of chelating agents of the Mn(II) and/or Zn(II) salts used because these agents tend to inhibit the oxidation of the colouring material precursors.

The dye compositions of the invention preferably have a pH which varies from 3 to 12, and preferably from 6 to 9 and is typically of the order of 8. This pH, close to neutrality, associated with the absence of the use of peroxides makes it possible to use these compositions for the coloration of sensitive scalps. This pH is adjusted by the use of acidifying or basifying agents well known in the state of the art of dyeing keratin fibres.

Of the basifying agents mention may be made, as examples, of ammonia, the alkali carbonates, the alkanolamines such as the mono-, di- and triethanolamines as well as their derivatives, sodium or potassium hydroxides and the compounds of the following formula (V):

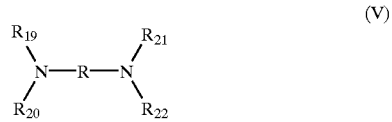

in which:
R is a propylene residue optionally substituted by a hydroxyl group or a $C_1$–$C_4$ alkyl radical; and
$R_{19}$, $R_{20}$, $R_{21}$ and $R_{22}$, identical or different, represent hydrogen, a $C_1$–$C_4$ alkyl radical or $C_1$–$C_4$ hydroxyalkyl radical.

The acidifying agents are conventionally, as examples, mineral or organic acids like hydrochloric acid, orthophosphoric acid, carboxylic acids such as tartaric acid, citric acid, lactic acid, or sulfonic acids.

In order to reveal the coloration of the compositions according to the invention, it is sufficient to place the composition containing at least one colouring material precursor and one oxidation base and an efficacious quantity of the catalytic system according to the invention in the presence of an oxidising medium such as a medium containing oxygen (for example the oxygen of the air).

The compositions according to the invention are useful for the coloration of keratin fibres such as hair, eyelashes, eyebrows and bristles.

For the coloration of keratin fibres, different processes of application of the compositions according to the invention can be used.

According to a first process, a composition containing all of the ingredients of the composition of the invention is applied to the keratin fibres in the presence of oxygen, for example the oxygen of the air.

According to a second process, it is possible in the first place to apply to the keratin fibres a first composition of one or more colouring material precursors in a physiologically acceptable medium, then to this first composition, is added a second composition containing the catalytic system in a physiologically acceptable medium which in the presence of oxygen will reveal the coloration, the oxidation base(s) being contained in one or other of the compositions.

Quite obviously, the order of application of the compositions can be reversed.

The compositions can be applied by any known means, in particular by spraying.

The coloration of the composition can be determined by the choice of the colouring material precursors.

The compositions according to the invention are available and are packaged in different forms.

According to a first embodiment, the compositions according to the invention can be packaged in the form of an aerosol in a single compartment in which are located the composition containing the colouring material precursor(s), the oxidation base(s), the catalytic system and a conventional inert propellant gas such as nitrogen, a saturated hydrocarbon like isopropane or a halogenated hydrocarbon.

In a second embodiment, the composition according to the invention can be packaged in the form of a kit comprising two distinct containers, one for the base composition containing the colouring material precursor(s) and the oxidation base(s), the other for the catalytic system, the base composition and the catalytic system being mixed or applied successively at the time of use.

In a third embodiment, the composition according to the invention can also be packaged in the form of a kit comprising two distinct containers, one for the base composition containing the colouring material precursor(s), the other for the catalytic system and the oxidation base(s), the base composition and the catalytic system being mixed or applied successively at the time of use.

In a fourth embodiment, the composition may be contained in a one-compartment pump system without intake of air or in a two-compartment pump system, the colouring material precursor being in one compartment and the catalytic system in the other, the oxidation base(s) being contained in one or the other of these compartments.

In a fifth embodiment, the composition according to the invention is available in the form of one or more sachets impermeable to oxygen. This or these sachets will advantageously be sachets made of aluminium.

If the composition according to the invention is available in the form of a single sachet, this latter will contain the colouring material precursor(s), the oxidation base(s) and the catalytic system.

If the composition according to the invention is available in the form of two sachets, the first sachet will contain the catalytic system and the second sachet will contain the colouring material precursor(s), the oxidation base(s) being contained in either the first sachet or the second sachet.

EXAMPLE

Coloration tests have been performed on locks of hair. For that purpose, several formulations of the coloration composition according to the invention have been prepared. The formulations are given in the Table below.

The diaminopyrazole corresponds to formula (VI):

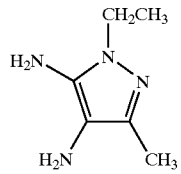

(VI)

| Formulation N° | First colouring material precursor | | Oxidation base | | Catalytic system [MnCl$_2$ + NaHCO$_3$] | | |
|---|---|---|---|---|---|---|---|
| | Nature | Quantity | Nature | Quantity | Concentration MnCl$_2$ | Concentration NaHCO$_3$ | Quantity |
| 1 | catechol | 25 mg | paraphenylene-diamine | 25 mg | 10 mM/l | 1 M | 10 ml |
| 2 | catechol | 25 mg | paraaminophenol | 25 mg | 10 mM/l | 1 M | 10 ml |
| 3 | catechol | 25 mg | diaminopyrazole | 25 mg | 10 mM/l | 1 M | 10 ml |

Each of the formulations 1 to 3 was applied to a lock of hair of a natural grey colour. The locks were allowed to incubate for one hour, then they were rinsed with hot tap water.

The following results recapitulated in Table 2 were obtained with the formulations 1 to 3:

TABLE 2

| Formulation n° | Colour |
|---|---|
| 1 | brownish-red |
| 2 | light brown |
| 3 | dark brown |

The combination of ortho-diphenols with an oxidation base gives novel colour tints.

Finally, a pH close to neutrality of the compositions combined with the absence of peroxides makes it possible to contemplate their use for the colouring of hair of people with sensitive scalps.

The priority document of the present application, French Application No. FR 00 15695, filed Dec. 4, 2000, is incorporated herein by reference.

What is claimed is:

1. A composition for the coloration of keratin fibres comprising, in a physiologically acceptable medium, an efficacious quantity of at least one colouring material precursor selected from the compounds containing at least one aromatic ring having at least two hydroxyl groups borne by two adjacent carbon atoms of the aromatic ring, an efficacious quantity of at least one oxidation base of the para or ortho type selected from the aromatic amines, and an efficacious quantity of a catalytic system comprising a first constituent selected from the group consisting of salts and oxides of Mn(II) and/or Zn(II) and their mixtures, and a second constituent selected from the group consisting of alkali hydrogen carbonates, alkaline earth hydrogen carbonates and their mixtures, the proportions of the first constituent and the second constituent being such that:

$$\frac{[Mn(II)]}{[HCO_3]} \leq 1 \text{ with } [Mn(II)] \neq 0$$

where [(Mn(II)], [Zn(II)] and [HCO$_3$] respectively represent the molar concentrations of Mn(II), Zn(II) and HCO$_3$ wherein $$\frac{[Zn(II)]}{[HCO_3]} \leq 1 \text{ with } [Zn(II)] \neq 0 \text{ and}$$

$$\frac{[Mn(II)] + [Zn(II)]}{[HCO_3]} \leq 1 \text{ with } [Mn(II)] \text{ and } [Zn(II)] \neq 0.$$

2. The composition according to claim 1, wherein the ratio $$\frac{[Mn(II)]}{[HCO_3]}$$

varies from $10^{-5}$ to $10^{-1}$.

3. The composition according to claim 1 or 2, wherein the ratio $$\frac{[Zn(II)]}{[HCO3]}$$

varies from $10^{-4}$ to $<1$.

4. The composition according to claim 1, wherein the ratio $$\frac{[Mn(II)] + [Zn(II)]}{[HCO_3]}$$

varies from $10^{-5}$ to $10^{-1}$.

5. The composition according to claim 1, wherein the salts of Mn(II) and Zn(II) are selected from the group consisting of chloride, fluoride, iodide, sulfate, phosphate, nitrate, perchlorate, carboxylic acid salts and their mixtures.

6. The composition according to claim 5, wherein the salt of Mn(II) and/or Zn(II) is a chloride.

7. The composition according to claim 5, wherein the salts of carboxylic acids are salts of hydroxylated carboxylic acids.

8. The composition according to claim 7, wherein the hydroxylated carboxylic acid salt is gluconate.

9. The composition according to claim 1, wherein the hydrogen carbonate is selected from the group consisting of sodium hydrogen carbonate, potassium hydrogen carbonate, magnesium hydrogen carbonate, calcium hydrogen carbonate and their mixtures.

10. The composition according to claim 1, wherein the aromatic ring bearing at least two hydroxyl groups on two adjacent carbon atoms of the first colouring material precursor is a benzene ring or a condensed aromatic ring.

11. The composition according to claim 10, wherein the colouring material precursor is a compound of formula (I):

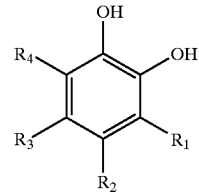

in which the substituents R$_1$ to R$_4$, are identical or different, and represent hydrogen, halogen, hydroxyl, carboxyl, alkyl carboxylate, optionally substituted amino, optionally substituted linear or branched alkyl, optionally substituted linear or branched alkenyl, optionally substituted cycloalkyl, alkoxy, alkoxyalkyl, alkoxyaryl, the aryl group being optionally substituted, aryl, substituted aryl, optionally substituted heterocyclic radical, a radical optionally containing one or more silicon atoms in which two of the substituents R$_1$ to R$_4$ form together a saturated or unsaturated ring optionally containing one mor more heteroatoms and optionally condensed with one or more saturated or unsaturated rings optionally containing one or more heteroatoms.

12. The composition according to claim 1, wherein the colouring material precursor is selected from the group consisting of flavanols, anthocyanidines, anthocyanines, hydroxybenzoates, flavones, iridoids, each of which are optionally glycosylated and/or in the form of oligomers, hydroxystilbenes, optionally glycosylated, 3,4-dihydroxyphenylalanine and its derivatives, 2,3-dihydroxyphenylalanine and its derivatives, 4,5-dihydroxyphenylalanine and its derivatives, 4,5-dihydroxyindole and its derivatives, 5,6-dihydroxyindole and its derivatives, 6,7-dihydroxyindole and its derivatives, 2,3-dihydroxyindole and its derivatives, dihydroxycinnamates, hydroxycoumarins, hydroxyisocoumarins, hydroxycoumarones, hydroxyisocoumarones, hydroxychalcones, hydroxychromones, anthocyans, quinones, hydroxyxanthones, 1,2-dihydroxybenzenes, 1,2,4-trihydroxybenzenes, 1,2,3-trihydroxybenzenes, 2,4,5-trihydroxytoluene, 5,6-dihydroxyindoline, and mixtures of two or more of the preceding compounds.

13. The composition according to claim 1, wherein the colouring material precursor is selected from the group consisting of extracts of plants, fruits, citrus fruits, vegetables and their mixtures.

14. The composition according to claim 13, wherein the colouring material precursor is selected from the extracts of tea, grape, apple, banana, potato and their mixtures.

15. The composition according to claim 1, wherein the colouring material precursor is present to the extent of at least 0.001% of the total weight of the composition.

16. The composition according to claim 1, wherein the oxidation base may be selected from the group consisting of ortho and para phenylenediamines, double bases, ortho and para aminophenols, heterocyclic bases as well as addition salts of all of these compounds with an acid.

17. The composition according to claim 16, wherein the oxidation base is selected from the para-phenylenediamines corresponding to formula (II):

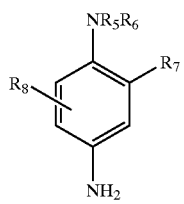

in which:
R$_5$ represents hydrogen, C$_1$–C$_4$ alkyl, C$_1$–C$_4$ monohydroxyalkyl, C$_2$–C$_4$ polyhydroxyalkyl, C$_1$–C$_4$ alkoxy C$_1$–C$_4$ alkyl, C$_1$–C$_4$ alkyl, substituted by a nitrogen-containing group, phenyl or 4'-aminophenyl;

R$_6$ represents hydrogen, C$_1$–C$_4$ alkyl, C$_1$–C$_4$ monohydroxyalkyl or C$_2$–C$_4$ polyhydroxyalkyl, C$_1$–C$_4$ alkoxy C$_1$–C$_4$ alkyl or C$_1$–C$_4$ alkyl, substituted by a nitrogen-containing group;

R$_7$ represents hydrogen, halogen, chlorine, a C$_1$–C$_4$ alkyl radical, sulfo, carboxy, C$_1$–C$_4$ monohydroxyalkyl or C$_1$–C$_4$ hydroxyalkoxy, C$_1$–C$_4$ acetylaminoalkoxy, C$_1$–C$_4$ mesylaminoalkoxy or C$_1$–C$_4$ carbamoylaminoalkoxy;

R$_8$ represents hydrogen, halogen or C$_1$–C$_4$ alkyl;

R$_5$ and R$_6$ may also form with the nitrogen atom which bears them a 5 or 6 membered nitrogen-containing heterocycle, optionally substituted by one or more alkyl, hydroxy or ureido groups.

18. The composition according to claim 17, wherein the para-phenylenediamines are selected from the group consisting of para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-diethyl-para-phenylenediamine, 2,3-dimethyl-para-phenylenediamine, N,N bis-(β-hydroxyethyl)-para-phenylenediamine, 2-chloro-para-phenylenediamine, and their addition salts with an acid.

19. The composition according to claim 16, wherein the double bases are selected from compounds corresponding to formula (III):

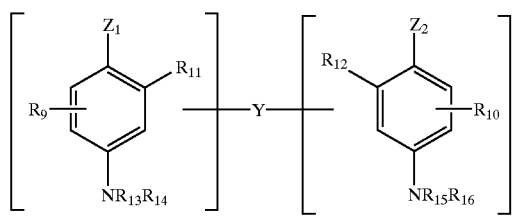

in which:
Z$_1$ and Z$_2$, identical or different, represent a hydroxyl or —NH$_2$ radical which may be substituted by a C$_1$–C$_4$ alkyl radical or by a linking arm Y;

the linking arm Y represents an alkylene chain comprising from 1 to 14 linear or branched carbon atoms which may be interrupted or terminated by one or more nitrogen-containing groups and/or by one or more heteroatoms such as oxygen, sulfur or nitrogen atoms, and optionally substituted by one or more hydroxyl or C$_1$–C$_6$ alkoxy radicals;

R$_9$ and R$_{10}$ represent hydrogen or halogen, a C$_1$–C$_4$ alkyl radical, C$_1$–C$_4$ monohydroxyalkyl, C$_2$–C$_4$ polyhydroxyalkyl, C$_1$–C$_4$ aminoalkyl or a linking arm Y;

R$_{11}$, R$_{12}$, R$_{13}$, R$_{14}$, R$_{15}$ and R$_{16}$, identical or different, represent hydrogen, a linking arm Y or a C$_1$–C$_4$ alkyl radical; it being understood that the compounds of formula (III) only bear a single linking arm Y per molecule.

20. The composition according to claim 19, wherein the double bases are selected from the group consisting of N,N'-bis-(β-hydroxyethyl) N,N'-bis-(4'-aminophenyl) 1,3-diaminopropanol, N,N'-bis-(β-hydroxyethyl) N,N'-bis-(4'-aminophenyl) ethylenediamine, N,N'-bis-(4'-aminophenyl) tetramethylenediamine, N,N'-bis-(β-hydroxyethyl) N,N'-bis-(4'-aminophenyl) tetramethylenediamine, N,N'-bis-(4'-methyl-aminophenyl) tetramethylenediamine, N,N'-bis-(ethyl) N,N'-bis-(4'-amino, 3-methylphenyl) ethylenediamine, 1,8-bis-(2,5-diaminophenoxy)-3,5-dioxo-octane, and their addition salts with an acid.

21. The composition according to claim 16, wherein the oxidation base is selected from the para-aminophenols corresponding to formula (IV):

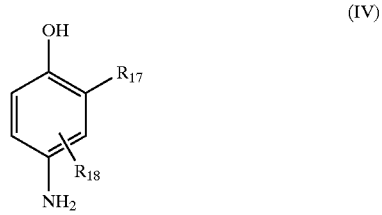

in which:
R$_{17}$ represents hydrogen, halogen, fluorine, C$_1$–C$_4$ alkyl, C$_1$–C$_4$ monohydroxyalkyl, C$_1$–C$_4$ alkoxy C$_1$–C$_4$ alkyl or C$_1$–C$_4$ aminoalkyl, or C$_1$–C$_4$ hydroxyalkyl C$_1$–C$_4$ aminoalkyl, and R$_{18}$ represents hydrogen, halogen, fluorine, C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or C$_1$–C$_4$ hydroxyalkyl C$_1$–C$_4$ alkyl.

22. The composition according to claim 21; wherein the para-aminophenols are selected from the para-aminophenol, 4-amino-3-methyl-phenol, 4-amino-3-fluoro-phenol, 4-amino-3-hydroxymethyl phenol, 4-amino-2-methyl phenol, 4-amino-2-methoxymethyl phenol, 4-amino-2-aminomethyl phenol, 4-amino-2-(13-hydroxyethyl-aminomethyl) phenol, and their addition salts with an acid.

23. The composition according to claim 16, wherein the oxidation base is an ortho-aminophenol selected from the group consisting of 2-aminophenol, 2-amino-1-hydroxy-5-methyl-benzene, 2-amino-1-hydroxy-6-methyl-benzene, 5-acetamido-2-amino-phenol, and their addition salts with an acid.

24. The composition according to claim 16, wherein the oxidation base is a heterocyclic base selected from the group consisting of pyridine derivatives, pyrimidine derivatives, pyrazole derivatives and their addition salts with an acid.

25. The composition according to claim 24, wherein the pyridine derivatives are selected from the group consisting of 2,5-diamino pyridine, 2-(4-methoxyphenyl) amino-3-amino-pyridine, 2,3-diamino-6-methoxy pyridine, 2-(β-methoxyethyl) amino-3-amino-6-methoxy pyridine, 3,4-diamino pyridine and their addition salts with an acid.

26. The composition according to claim 24; wherein the pyrimidine derivatives are selected from the group consisting of 2,4,5,6-tetra-aminopyrimidine, 4-hydroxy-2,5,6-triaminopyrimidine, 2-hydroxy-4,5,6-triaminopyrimidine, 2,4-dihyroxy-5,6 diaminopyrimidine, 2,5,6- triaminopyrimidine, pyrazolo-pyrimidine derivatives, pyrazolo-[1,5-a]-pyrimidine-3,7-diamine; 2,5-dimethyl-pyrazolo-[1,5-a]-pyrimidine-3,7-diamine, pyrazolo-[1,5-a]-pyrimidine-3,5-diamine; 2,7-dimethyl-pyrazolo-[1,5-a]-pyrimidine-3,5-diamine; 3-amino-pyrazolo-[1,5-a]-pyrimidin-7-ol; 3-amino-pyrazolo-[1,5-a]-pyrimidin-5-ol; 2-(3-amino-pyrazolo-[1,5-a]-pyrimidin-7-ylamino)-ethanol; 2-(7-amino-pyrazolo-[1,5-a]-pyrimidin-3-ylamino)-ethanol; 2-[(3-amino-pyrazolo-[1,5-a]-pyrimidin-7-yl)-(2-hydroxy-ethyl-amino)-ethanol; 2-[(7-amino-pyrazolo-[1,5-a]-pyrimidin-3-yl)-(2-hydroxy-ethyl-amino)-ethanol; 5,6-dimethyl-pyrazolo-[1,5-a]-pyrimidine-3,7-diamine; 2,6-dimethyl-pyrazolo-[1,5-a]-pyrimidine-3,7-diamine; 2,5, N7, N7-tetramethyl-pyrazolo-[1,5-a]-pyrimidine-3,7-diamine; 3-amino-5-methyl-7-imidazolylpropylamiflo pyrazolo-[1,5-a]-pyrimidine; and their addition salts and their tautomeric forms, when a tautomeric equilibrium exists.

27. The composition according to claim 24, wherein the pyrazole derivatives are selected from the group consisting of 4,5-diamino-1-methyl-pyrazole, 3,4-2 diamino-pyrazole, 4,5-diamino-1-(4'-chlorobenzyl)-pyrazole, 4,5-diamino-1,3-dimethylpyrazole, 4,5-diamino-3-methyl-1-phenyl pyrazole, 4,5-diamino-1-methyl-3-phenyl pyrazole, 4-amino-1,3-dimethyl-5-hydrazino-pyrazole, 1-benzyl-4,5-diamino-3-methyl pyrazole, 4,5-diamino-3-tert-butyl-1-methyl pyrazole, 4,5-diamino-1-tert-butyl-3-methyl pyrazole, 4,5-diamino-1-(β-hydroxyethyl)-3-methyl pyrazole, 4,5-diamino-1-(β-hydroxyethyl)-pyrazole, 4,5-diamino-1-ethyl-3-methyl pyrazole, 4,5-diamino-1-ethyl-3-(4'-methoxyphenyl)-pyrazole, 4,5-diamino-1-ethyl-3-hydroxymethyl pyrazole, 4,5-diamino-3-hydroxymethyl-1-methyl pyrazole, 4,5-diamino-3-hydroxymethyl-1-isopropyl pyrazole, 4,5-diamino-3-methyl-1-isopropyl pyrazole, 4-amino-5-(2'-aminoethyl)amino-1,3-dimethyl pyrazole, 3,4,5-triamino pyrazole, 1-methyl-3,4,5-triamino-pyrazole, 3,5-diamino-1-methyl-4-methylamino-pyrazole, and 3,5-diamino-4-(β-hydroxyethyl)amino-1-methyl-pyrazole.

28. The composition according to claim F, wherein the oxidation base represents from 0.0005 to 12% by weight of the total weight of the composition.

29. The composition according to claim 1, wherein the physiologically acceptable medium is a solubilizing medium.

30. The composition according to claim 1, wherein the physiologically acceptable medium comprises a solvent or mixture of solvents.

31. The composition according to claim 30, wherein the solvent is selected from the group consisting of water, alcohols, polyols, polyol ethers and their mixtures.

32. The composition according to claim 31, wherein the alcohol is an alkanol or an alkanediol.

33. The composition according to claim 31 or 32, wherein the solvent is a water/alcohol mixture.

34. The composition according to claim 33, wherein the alcohol represents up to 80% by weight of the mixture.

35. The composition according to claim 1, wherein said composition further comprises one or more couplers selected from the group consisting of meta-aminophenols, meta-phenylenediamines, meta-diphenols, naphthols and heterocyclic couplers, indole derivatives, indoline derivatives, sesamol and its derivatives, pyridine derivatives, pyrazolotriazole derivatives, pyrazolones, indazoles, benzimidazoles, benzothiazoles, benoxazoles, 1,3-benzodioxoles, quinolines and their addition salts with an acid.

36. The composition according to claim 35, wherein the couplers are selected from the group consisting of 2,4-diamino-1-(β-hydroxyethyloxy) benzene, 2-methyl 5-amino phenol, 5-N-(β-hydroxyethyl) amino 2-methyl phenol, 3-amino phenol, 1,3-dihydroxybenzene, 1,3-dihydroxy 2-methyl benzene, 4-chioro 1,3-dihydroxybenzene, 2-amino 4-(β-hydroxyethylamino) 1-methoxybenzene, 1,3-diaminobenzene, 1,3-bis-(2,4-diaminophenoxy) propane, sesamol, 1-amino-2-methoxy-4,5-methylenedioxy beuzene, α-naphthol, 6-hydroxyindole, 4-hydroxyindoline, 4-hydroxy N-methyl indoline, 6-hydroxyindoline, 2,6-dihydroxy 4-methyl pyridine, 1-H 3-methyl pyrazole 5-one, 1-phenyl 3-methyl pyrazol-5-one, 2-amino 3-hydroxypyridine, 3,6-dimethyl pyrazolo-[3,2-c]-1,2,4-triazole, 2,6-dimethyl-pyrazolo-[1,5-b]-1,2,4-triazole and their addition salts with an acid.

37. The composition according to claim 35 or 36, wherein the one or more couplers represent from 0.0001 to 15% by weight of the total weighty of the composition.

38. The composition according to claim 1, wherein said composition is free of any chelating agent for the Mn(II) and/or Zn(II) salt(s).

39. The composition according to claim 1, wherein said composition is packaged in the form of an aerosol or a pump system without intake of air.

40. The composition according to claim 1, wherein said composition is in the form of two separate constituents, a first constituent comprising the catalytic system and the oxidation base, dissolved in a physiologically acceptable medium, and a second constituent comprising the colouring material precursor dissolved in a physiologically acceptable medium.

41. The composition according to claim 1, wherein said composition is in the form of two separate constituents, a first constituent comprising the catalytic system dissolved in a physiologically acceptable medium, and a second constituent comprising the colouring material precursor and the oxidation base dissolved in a physiologically acceptable medium.

42. The composition according to claims 40 or 41, wherein said composition is packaged in a pump system with two distinct compartments, the colouring material precursor(s) being in one compartment and the catalytic system being in the other compartment, and the oxidation base(s) being in one or other of these two compartments.

43. The composition according to claim 1, wherein said composition is packaged in the form of one or more sachets impermeable to oxygen.

44. The composition according to claim 43, wherein said composition is packaged in the form of two sachets impermeable to oxygen:
  a first sachet containing the catalytic system and the oxidation base(s) and a second sachet containing the colouring material precursor, or
  a first sachet containing the catalytic system and a second sachet containing the colouring material precursor(s) and the oxidation base(s).

45. The process for the coloration of keratin fibres, comprising applying to skin and/or keratin fibres a layer of a composition according to claim 1.

46. The process according to claim 45, comprising applying to the keratin fibres a first base composition containing one mor more colouring material precursor(s) in a physiologically acceptable medium, then by applying a composition containing the catalytic system in a physiologically acceptable medium, or vice versa, the oxidation base(s) being either contained in the base composition or combined with the catalytic system.

47. The process according to claims 45 or 46, wherein the compositions are applied by spraying.

48. The composition according to claim 2, wherein the ratio of $$\frac{[Mn(II)]}{[HCO_3]}$$

varies from $10^{-3}$ to $10^{-2}$.

49. The composition according to claim 2, wherein the ratio $$\frac{[Mn(II)]}{[HCO_3]}$$

is of order of $5 \times 10^{-3}$.

50. The composition according to claim 3, wherein the ratio $$\frac{[Zn(II)]}{[HCO3]}$$

varies from $10^{-3}$ to $<1$.

51. The composition according to claim 3, wherein the ratio $$\frac{[Zn(II)]}{[HCO3]}$$

is of the order of $5 \times 10^{-1}$.

52. The composition according to claim 4, wherein the ratio $$\frac{[Mn(II)] + [Zn(II)]}{[HCO_3]}$$

varies from $10^{-3}$ to $10^{-2}$.

53. The composition according to claim 28, wherein the oxidation base represents from 0.005 to 8% by weight of the total weight of the composition.

54. The composition according to claim 29, wherein the physiologically acceptable medium is a solubilizing medium with bacteriostatic properties.

55. The composition according to claim 34, wherein the alcohol represents 1 to 50% by weight of the mixture.

56. The composition according to claim 34, wherein the alcohol represents 5 to 20% by weight of the mixture.

57. The composition according to claim 37, wherein the one or more couplers represent 0.001 to 10% by weight of the total weight of the composition.

* * * * *

UNITED STATES PATENT AND TRADEMARK OFFICE
CERTIFICATE OF CORRECTION

PATENT NO. : 6,723,136 B2
DATED : April 20, 2004
INVENTOR(S) : Francis Pruche

It is certified that error appears in the above-identified patent and that said Letters Patent is hereby corrected as shown below:

Column 16,
Line 23, "mor" should read -- or --

Column 18,
Line 45, "13" should read -- ($\beta$ --

Column 19,
Line 20, "3,4-2 diamino" should read -- 3,4-diamino --
Line 38, "Claim F" should read -- Claim 1 --

Column 20,
Line 4, "chioro" should read -- chloro --
Line 7, "beuzene" should read -- benzene --

Signed and Sealed this

Twenty-eighth Day of December, 2004

JON W. DUDAS
*Director of the United States Patent and Trademark Office*